United States Patent
Konieczynski et al.

(10) Patent No.: US 11,026,725 B2
(45) Date of Patent: *Jun. 8, 2021

(54) HYBRID SPINAL PLATES

(71) Applicant: DePuy Synthes Products, Inc., Raynham, MA (US)

(72) Inventors: David D. Konieczynski, Needham, MA (US); Michael Jacene, Blackstone, MA (US); Michael Gorhan, Mansfield, MA (US); Eric D. Kolb, Milton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 189 days.

This patent is subject to a terminal disclaimer.

(21) Appl. No.: 15/592,357

(22) Filed: May 11, 2017

(65) Prior Publication Data
US 2017/0238974 A1  Aug. 24, 2017

Related U.S. Application Data

(60) Division of application No. 14/562,804, filed on Dec. 8, 2014, now abandoned, which is a continuation of
(Continued)

(51) Int. Cl.
*A61B 17/70* (2006.01)
*A61B 17/80* (2006.01)

(52) U.S. Cl.
CPC ...... *A61B 17/7059* (2013.01); *A61B 17/8042* (2013.01); *A61B 17/8047* (2013.01); *A61B 17/8052* (2013.01)

(58) Field of Classification Search
None
See application file for complete search history.

(56) References Cited

U.S. PATENT DOCUMENTS

| 2,486,303 A | 10/1949 | Longfellow |
| 4,388,921 A | 6/1983 | Sutter et al. |

(Continued)

FOREIGN PATENT DOCUMENTS

| EP | 0897697 A1 | 2/1999 |
| EP | 1 169 971 A2 | 1/2002 |

(Continued)

OTHER PUBLICATIONS

"Atlantis Vision® Anterior Cervical Plate System" at least partially dated 2003, retrieved from http://www.medtronicsofamordanek.com/stripcontent.php?parent_file=/atlantis-vision.html&printed=true on Mar. 21, 2005, 2 pages.

(Continued)

*Primary Examiner* — Samuel S Hanna
(74) *Attorney, Agent, or Firm* — Nutter McClennen & Fish LLP

(57) ABSTRACT

Various spinal plating systems for use in treating spinal pathologies are provided. In certain exemplary embodiments, the spinal plating systems can be configured to allow a surgeon to select a bone screw construct having a particular range of motion for attaching a spinal plate to bone as needed based on the intended use. In one exemplary embodiment, the spinal plating system includes a first bone screw that is polyaxially movable relative to the spinal plate, and a second bone screw that has a range of motion that is substantially limited to a single plane.

8 Claims, 10 Drawing Sheets

Related U.S. Application Data application No. 13/049,147, filed on Mar. 16, 2011, now Pat. No. 8,940,025, which is a continuation of application No. 10/904,984, filed on Dec. 8, 2004, now Pat. No. 7,931,678.

(56) References Cited

U.S. PATENT DOCUMENTS

| | | |
|---|---|---|
| 4,488,425 A | 12/1984 | Meikle |
| 4,651,724 A | 3/1987 | Berentey et al. |
| 4,696,290 A | 9/1987 | Steffee |
| 5,085,660 A | 2/1992 | Lin |
| 5,151,103 A | 9/1992 | Tepic et al. |
| 5,261,910 A | 11/1993 | Warden et al. |
| 5,275,601 A | 1/1994 | Gogolewski et al. |
| 5,364,399 A | 11/1994 | Lowery et al. |
| 5,423,826 A | 6/1995 | Coates et al. |
| 5,534,027 A | 7/1996 | Hodorek |
| 5,549,612 A | 8/1996 | Yapp et al. |
| 5,578,034 A | 11/1996 | Estes |
| 5,601,553 A | 2/1997 | Trebing et al. |
| 5,607,428 A | 3/1997 | Lin |
| 5,616,142 A | 4/1997 | Yuan et al. |
| 5,616,144 A | 4/1997 | Yapp et al. |
| 5,651,283 A | 7/1997 | Runciman et al. |
| 5,676,666 A | 10/1997 | Oxland et al. |
| 5,735,853 A | 4/1998 | Olerud |
| 5,807,396 A | 9/1998 | Raveh |
| 5,851,207 A | 12/1998 | Cesarone |
| 5,876,402 A | 3/1999 | Errico et al. |
| 5,904,683 A | 5/1999 | Pohndorf et al. |
| 5,931,838 A | 8/1999 | Vito |
| 5,951,558 A | 9/1999 | Fiz |
| 5,954,722 A | 9/1999 | Bono |
| 5,964,762 A | 10/1999 | Biedermann et al. |
| 6,017,345 A | 1/2000 | Richelsoph |
| 6,039,740 A | 3/2000 | Olerud et al. |
| 6,066,175 A | 5/2000 | Henderson et al. |
| 6,106,527 A | 8/2000 | Wu et al. |
| 6,139,550 A | 10/2000 | Michelson |
| 6,152,927 A | 11/2000 | Farris et al. |
| 6,159,213 A | 12/2000 | Rogozinski |
| 6,193,721 B1 | 2/2001 | Michelson |
| 6,224,602 B1 | 5/2001 | Hayes |
| 6,235,033 B1 | 5/2001 | Brace et al. |
| 6,235,034 B1 | 5/2001 | Bray |
| 6,241,731 B1 | 6/2001 | Fiz et al. |
| 6,258,098 B1 | 7/2001 | Taylor et al. |
| 6,261,291 B1 | 7/2001 | Talaber et al. |
| 6,261,296 B1 | 7/2001 | Aebi et al. |
| 6,273,889 B1 | 8/2001 | Richelsoph |
| 6,293,949 B1 | 9/2001 | Justis et al. |
| 6,306,136 B1 | 10/2001 | Baccelli |
| 6,306,139 B1 | 10/2001 | Fuentes et al. |
| 6,328,738 B1 | 12/2001 | Suddaby |
| 6,331,179 B1 | 12/2001 | Freid et al. |
| 6,342,057 B1 | 1/2002 | Brace et al. |
| 6,379,364 B1 | 4/2002 | Brace et al. |
| 6,398,783 B1 | 6/2002 | Michelson |
| 6,402,756 B1 | 6/2002 | Ralph et al. |
| 6,413,259 B1 | 7/2002 | Lyons et al. |
| 6,428,542 B1 | 8/2002 | Michelson |
| 6,454,771 B1 | 9/2002 | Michelson |
| 6,503,250 B2 | 1/2003 | Paul |
| 6,527,776 B1 | 3/2003 | Michelson |
| 6,533,786 B1 | 3/2003 | Needham et al. |
| 6,553,786 B1 | 4/2003 | Kwiat |
| 6,575,975 B2 | 6/2003 | Brace et al. |
| 6,595,993 B2 | 7/2003 | Donno et al. |
| 6,620,163 B1 | 9/2003 | Michelson |
| 6,623,486 B1 | 9/2003 | Weaver et al. |
| 6,652,525 B1 | 11/2003 | Assaker et al. |
| 6,669,700 B1 | 12/2003 | Farris et al. |
| 6,679,883 B2 | 1/2004 | Hawkes et al. |
| 6,692,503 B2 | 2/2004 | Foley et al. |
| 6,695,846 B2 | 2/2004 | Richelsoph et al. |
| 6,712,818 B1 | 3/2004 | Michelson |
| 6,755,833 B1 | 6/2004 | Paul et al. |
| 7,001,387 B2 | 2/2006 | Farris et al. |
| 7,001,389 B1 | 2/2006 | Navarro et al. |
| 7,931,678 B2 | 4/2011 | Konieczynski et al. |
| 8,940,025 B2 | 1/2015 | Konieczynski et al. |
| 2001/0047172 A1 | 11/2001 | Foley et al. |
| 2002/0016595 A1 | 2/2002 | Michelson |
| 2002/0055741 A1 | 5/2002 | Schlapfer et al. |
| 2002/0058939 A1 | 5/2002 | Wagner et al. |
| 2002/0143336 A1 | 10/2002 | Hearn |
| 2002/0147450 A1 | 10/2002 | LeHuec et al. |
| 2002/0156474 A1 | 10/2002 | Wack et al. |
| 2002/0183754 A1 | 12/2002 | Michelson |
| 2002/0183757 A1 | 12/2002 | Michelson |
| 2003/0040749 A1 | 2/2003 | Grabowski et al. |
| 2003/0083658 A1 | 5/2003 | Hawkes et al. |
| 2003/0083667 A1 | 5/2003 | Ralph et al. |
| 2003/0135213 A1 | 7/2003 | LeHuec et al. |
| 2003/0187440 A1 | 10/2003 | Richelsoph et al. |
| 2003/0187442 A1 | 10/2003 | Richelsoph et al. |
| 2003/0212399 A1 | 11/2003 | Dinh et al. |
| 2003/0225409 A1 | 12/2003 | Freid et al. |
| 2004/0006343 A1 | 1/2004 | Sevrain |
| 2004/0015169 A1 | 1/2004 | Gause |
| 2004/0015174 A1 | 1/2004 | Null et al. |
| 2004/0019353 A1 | 1/2004 | Freid et al. |
| 2004/0034352 A1 | 2/2004 | Needham et al. |
| 2004/0034354 A1 | 2/2004 | Paul |
| 2004/0034356 A1 | 2/2004 | LeHuec et al. |
| 2004/0039387 A1* | 2/2004 | Gause ............... A61B 17/1735 606/86 B |
| 2004/0087951 A1 | 5/2004 | Khalili |
| 2004/0097935 A1 | 5/2004 | Richelsoph et al. |
| 2004/0097950 A1 | 5/2004 | Foley et al. |
| 2004/0127896 A1 | 7/2004 | Lombardo et al. |
| 2004/0133205 A1 | 7/2004 | Thramann et al. |
| 2004/0186482 A1 | 9/2004 | Kolb et al. |
| 2004/0204716 A1 | 10/2004 | Fanger et al. |
| 2004/0204717 A1 | 10/2004 | Fanger et al. |
| 2004/0220572 A1 | 11/2004 | Michelson |
| 2004/0229348 A1 | 11/2004 | Kahlert et al. |
| 2004/0236335 A1* | 11/2004 | Michelson ............ A61B 17/863 623/17.11 |
| 2005/0015092 A1 | 1/2005 | Rathbun et al. |
| 2005/0033294 A1 | 2/2005 | Garden et al. |
| 2005/0038444 A1 | 2/2005 | Binder et al. |
| 2005/0043736 A1 | 2/2005 | Mathieu et al. |
| 2005/0131413 A1 | 6/2005 | O'Driscoll et al. |
| 2005/0154392 A1 | 7/2005 | Medoff et al. |
| 2006/0122602 A1 | 6/2006 | Konieczynski et al. |
| 2006/0122604 A1 | 6/2006 | Gorhan et al. |
| 2011/0190827 A1 | 8/2011 | Konieczynski et al. |
| 2015/0094764 A1 | 4/2015 | Konieczynski et al. |

FOREIGN PATENT DOCUMENTS

| | | |
|---|---|---|
| EP | 1221308 A1 | 7/2002 |
| EP | 1323390 | 7/2003 |
| FR | 2674118 A1 | 9/1992 |
| FR | 2785787 | 5/2000 |
| WO | 1996032071 A1 | 10/1996 |
| WO | 0234159 | 5/2002 |

OTHER PUBLICATIONS

Blackstone Medical, Inc., Cervical Systems: 3° Anterior Plate System (2005).

"Cervical Systems," Blacklstone Medical Inc., 2005, 1 page.

"Reflex® Hybrid: Anterior Cervical Plate System" dated 2005, retrieved from http://www.stryker.com/spine/products_cervical_reflex_hybrid.html on Mar. 21, 2005, 1 page.

European Search Report for EP App. No. 05826636.2 dated May 28, 2009 (13 pages).

European Examination Report for EP App. No. 05826636.2 dated Aug. 7, 2009 (13 pages).

(56) References Cited

OTHER PUBLICATIONS

European Examination Report for EP App. No. 05826636.2 dated Jul. 23, 2010 (3 pages).
European Search Report for EP App. No. 11176755.4 dated Oct. 17, 2011 (6 pages).
European Search Report for Application No. 11176755.4, dated Aug. 2, 2012.
Sofamor Danek, Atlantis Vision Anterior Cervical Plate System (Sep. 20, 2004).
Spinal Concepts, SC-Acufix Anterior Cervical Plating System (2003).
Stryker Spine, Cervical Products: Reflex Hybrid Plate (2005).
Surgical Polyaxial Anterior Technique Cervical Plate, PEAK, Howard S. An, M.D. et al., 1998, 15 pages.
International Search Report and Written Opinion for Application No. PCT/US05/41309, dated Aug. 24, 2006 (4 pages).

* cited by examiner

HYBRID SPINAL PLATES

CROSS-REFERENCE TO RELATED APPLICATIONS

The present application is a divisional of U.S. application Ser. No. 14/562,804 filed on Dec. 8, 2014 and entitled "Hybrid Spinal Plates," which is a continuation of U.S. application Ser. No. 13/049,147 filed on Mar. 16, 2011 and entitled "Hybrid Spinal Plates," now U.S. Pat. No. 8,940,025, which is a continuation of U.S. application Ser. No. 10/904,984 filed on Dec. 8, 2004 and entitled "Hybrid Spinal Plates," now U.S. Pat. No. 7,931,678, each of which is hereby incorporated by reference in its entirety.

BACKGROUND

For a number of known reasons, bone fixation devices are useful for promoting proper healing of injured or damaged vertebral bone segments caused by trauma, tumor growth, or degenerative disc disease. The fixation devices immobilize the injured bone segments to ensure the proper growth of new osseous tissue between the damaged segments. These types of bone fixation devices often include internal bracing and instrumentation to stabilize the spinal column to facilitate the efficient healing of the damaged area without deformity or instability, while minimizing any immobilization and post-operative care of the patient.

One such device is an osteosynthesis plate, more commonly referred to as a bone fixation plate, that can be used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The bone plate is placed against the damaged vertebral bodies and bone screws are used to secure the bone plate to the spine, usually with the bone screws being driven into the vertebral bodies.

Bone screws can be supported in a spinal plate in either a rigid or a semi-rigid fashion. In a rigid fashion, the bone screws are not permitted to move angularly relative to the plate. Conversely, in a semi-rigid fashion, the bone screws can move relative to the plate. The use of rigid and semi-rigid bone screws allow the surgeon to select the appropriate bone screw based on the particular treatment. While current plating systems can be effective, they typically require the use of different plates to obtain the desired bone screw fixation.

Accordingly, there remains a need for an improved plating system that allows the surgeon to use a single plate and to select between various types of bone screw fixation.

SUMMARY

Disclosed herein are various exemplary spinal plating systems for use in treating spinal pathologies. The spinal plating systems can be configured to allow a surgeon to select a bone screw construct having a particular range of motion for attaching a spinal plate to bone as needed based on the intended use. In one exemplary embodiment, the spinal plating system includes a first bone screw that is polyaxially movable relative to the spinal plate, and a second bone screw that has a range of motion that is substantially limited to a single plane.

While the exemplary spinal plating systems can include a spinal fixation plate having virtually any configuration, in one exemplary embodiment the spinal plate includes a thru-bore formed therein that is adapted to interchangeably receive a first bone engaging fastener such that a shank of the first bone engaging fastener is movable in more than one plane of motion relative to the spinal plate, and a second bone engaging fastener such that movement of a shank of the second bone engaging fastener relative to the spinal plate is substantially limited to a single plane of motion.

While the thru-bore in the spinal plate can have a variety of configurations, one exemplary thru-bore includes a proximal inner wall and a distal inner wall that differ in shape relative to one another. The proximal inner wall can, for example, be substantially symmetrical about a common axis of the thru-bore, and the distal inner wall can, for example, be substantially asymmetrical about the common axis. In another exemplary embodiment, at least a portion of the distal inner wall can extend at an angle relative to a central axis of the thru-bore. One exemplary angle is in the range of approximately 1° to approximately 10°. In another exemplary embodiment, the proximal inner wall of the thru-bore can be substantially spherical, and the distal inner wall of the thru-bore can be oblong. The oblong inner wall can have a maximum extent and a minimum extent that is less than the maximum extent. Where the spinal fixation plate includes opposed proximal and distal ends, and opposed lateral sides extending between the opposed proximal and distal ends, in one embodiment the minimum extent can extend in a proximal-distal direction, and the maximum extent can extend in a medial-lateral direction. In another embodiment, the maximum extent can extend in a proximal-distal direction, and the minimum extent can extend in a medial-lateral direction.

In yet another exemplary embodiment of the present invention, first and second bone engaging fasteners are provided having a shank with a head formed thereon and adapted to be received within a thru-bore in the spinal plate. The head of the second bone engaging fastener can be different from the head of the first bone engaging fastener such that the fasteners interact with a thru-bore in a spinal plate in two different orientations. While each bone engaging fastener can have a variety of configurations, in one exemplary embodiment the head of the first bone engaging fastener can have a distal portion with an extent that is substantially less than the maximum and minimum extents of a distal inner wall of the thru-bore formed in a spinal plate, and the head of the second bone engaging fastener can have a distal portion with an extent that is adapted to engage the minimum extent of the distal inner wall of the thru-bore.

In another embodiment, the spinal plate can include opposed proximal and distal ends and lateral sides extending between the proximal and distal ends. When a first bone engaging fastener is disposed within a thru-bore in the plate, a shank of the first bone engaging fastener can be movable in a proximal direction, a distal direction, a medial direction, a lateral direction, and combinations thereof. When a second bone engaging fastener is disposed within the thru-bore in the plate, a shank of the second bone engaging fastener can be substantially limited to movement in only one of a proximal direction, a distal direction, a medial direction, a lateral direction, a medial-lateral direction, and a proximal-distal direction.

An exemplary spinal plate having an insert disposed therein for receiving a first bone screw in a variable angle construct and a second bone screw in a limited angle construct is also provided. In another embodiment, the insert can be a ring-shaped member disposed within a thru-bore in the plate. The ring-shaped member can have a variety of configurations, for example it can include a split formed therein such that an extent of the ring-shaped member is adjustable. In one exemplary embodiment, the ring-shaped member can include an outer surface having a shape that complements a shape of an inner surface of the thru-bore, and an inner surface having at least a portion that is asymmetrical about an axis of the thru-bore in the insert. By way of non-limiting example, at least a portion of the inner surface of the thru-bore can have an oblong shape. In another embodiment, the ring-shaped member can be adapted to be disposed within the thru-bore in the spinal plate in a plurality of positions. The ring-shaped member can include an alignment mechanism adapted to align the ring-shaped member in one of the plurality of positions in the thru-bore in the spinal plate. By way of non-limiting example, the alignment mechanism can be at least one protrusion formed on an external surface of the ring-shaped member. The thru-bore in the spinal plate can include at least one corresponding detent formed therein for receiving the protrusion(s) on the ring-shaped member.

An exemplary spinal plating kit is also provided. In one embodiment, the spinal plating kit includes a first bone engaging fastener having a shank with a head formed thereon, a second bone engaging fastener having a shank with a head that differs from the head of the first bone engaging fastener, and a spinal plate having a thru-bore formed therein and adapted to selectively seat the head of the first and second bone engaging fasteners. At least a portion of the thru-bore can be substantially asymmetrical about an axis of the thru-bore such that the thru-bore is adapted to allow polyaxial movement of the shank of the first bone engaging fastener, and it is adapted to substantially limit movement of the shank of second bone engaging fastener to within a single plane of motion. In one exemplary embodiment, the thru-bore in the spinal plate can include a proximal portion that is adapted to selectively seat a proximal portion of the head of the first and second bone engaging fasteners, and a distal portion that is adapted to selectively seat a distal portion of the head of the first and second bone engaging fasteners. By way of non-limiting example, the proximal portion of the thru-bore can be substantially spherical and the distal portion of the thru-bore can be substantially oblong. In another exemplary embodiment, the head of the first bone engaging fastener can include a substantially spherical proximal portion and a distal portion, and the head of the distal portion of the second bone engaging fastener can include a substantially spherical proximal portion and a substantially cylindrical distal portion having a size that is greater than a size of the distal portion of the first bone engaging fastener such that the distal portion of the head of the second bone engaging fastener is adapted to engage at least a portion of the distal portion of the thru-bore.

Exemplary methods for implanting a spinal fixation plate are also provided. One exemplary methods includes positioning a spinal fixation plate against bone. The spinal fixation plate includes a thru-bore with an insert disposed therein. The insert can have a central opening formed therethrough and defining a single plane of motion of a bone engaging fastener to be received therein. The insert can then be rotated to orient the single plane of motion in a desired direction, and a bone engaging fastener can then be inserted through the insert to attach the spinal fixation plate to bone, wherein movement of a shank of the bone engaging fastener is limited to the desired direction of the single plane of motion.

DETAILED DESCRIPTION OF THE EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 7:
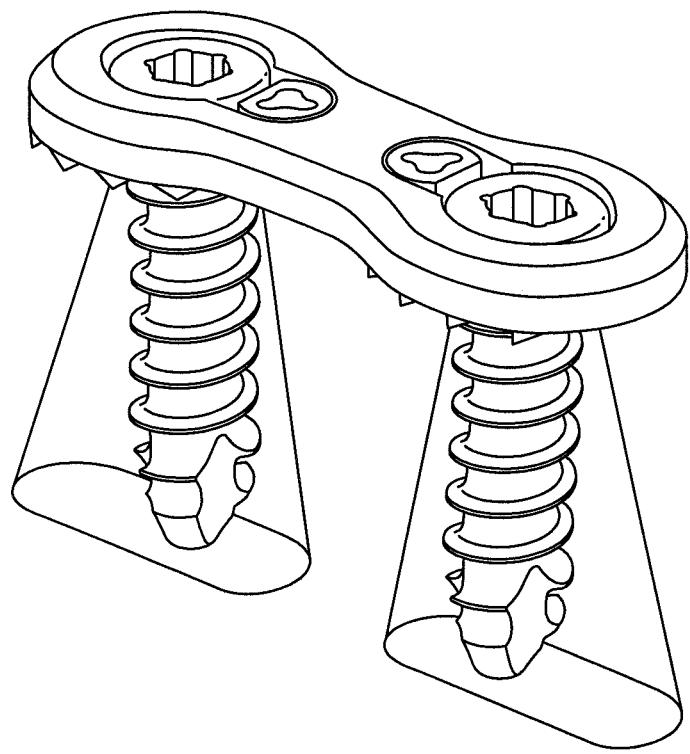
FIG. 7 is a perspective view of another exemplary embodiment of a spinal fixation plate.

In one exemplary embodiment, a spinal plating system is provided having a spinal plate with at least one thru-bore formed therein for selectively receiving at least two types of bone screws, thus allowing a surgeon to select an appropriate construct depending on the intended use. While various techniques can be used to achieve such a spinal plating system, and certain exemplary embodiments will be discussed in more detail below, FIGS. 1A-2C generally illustrate the functionality of one such exemplary spinal plating system having a spinal plate 10, a variable angle bone screw 20, and a limited angle bone screw 30. At the outset, one skilled in the art will understand that the spinal plate 10 and bone screws 20, 30 shown in FIGS. 1A-2C are merely shown for illustration purposes, and that the spinal plate 10 and bone screws 20, 30 can have virtually any configuration. By way of non-limiting example, FIG. 7 illustrates another exemplary embodiment of a spinal fixation plate that can include various features disclosed herein. A person skilled in the art will also appreciate that a variety of other fastening devices can be used in place of the bone screws 20, 30 to attach the spinal plate 10 to bone. While not shown or particularly described, the exemplary spinal plating systems disclosed herein can also include a rigid bone screw that is adapted to be disposed through a thru-bore in the plate at a fixed angle.

Figure 1A:
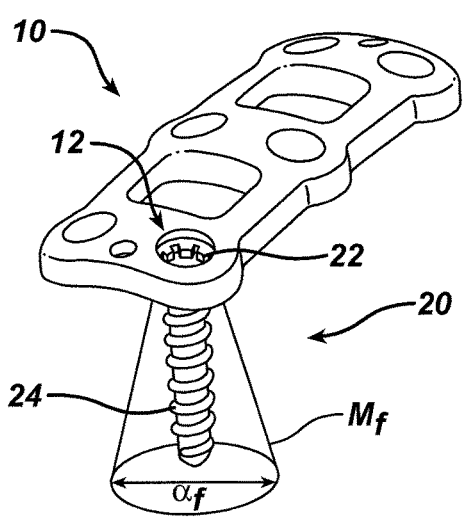
FIG. 1A is a perspective view of an exemplary embodiment of a spinal fixation plate having a bone screw disposed within a thru-bore formed therein and showing an exemplary range of motion of the bone screw.
Figure 1B:
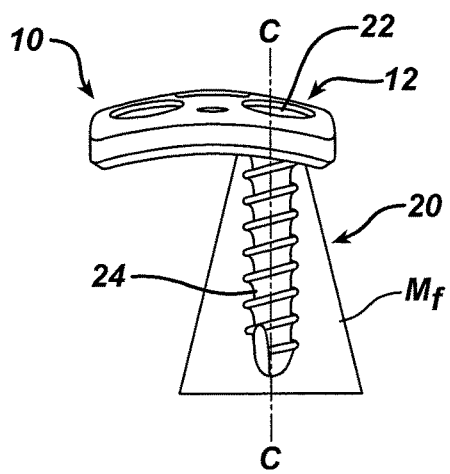
FIG. 1B is an end view of the spinal plate and bone screw shown in FIG. 1A.
Figure 1C:
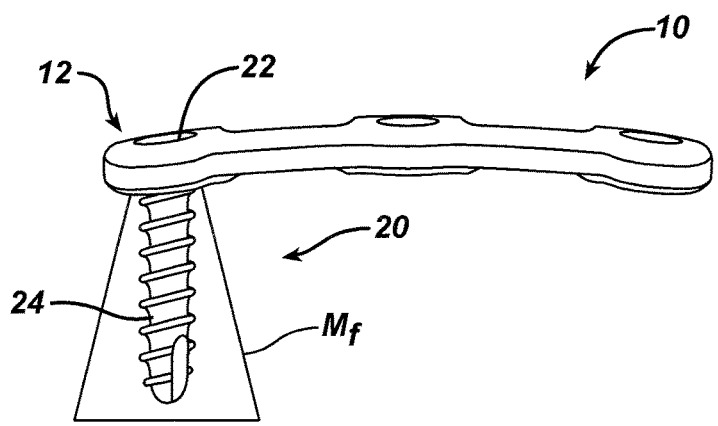
FIG. 1C is a side view of the spinal plate and bone screw shown in FIG. 1A.

Referring first to FIGS. 1A-1C, one exemplary embodiment of a variable angle bone screw 20 is shown disposed within a thru-bore 12 in a spinal plate 10. The bone screw 20, various exemplary embodiments of which will be discussed in more detail below, generally includes a head 22 and a shank 24 extending from the head 22. In this exemplary embodiment, when the shank 24 of the bone screw 20 is disposed through the thru-bore 12 in the plate 10 and the head 22 of the bone screw 20 is seated within the thru-bore 12, the shank 24 of the bone screw 20 can move polyaxially relative to the plate 10. In particular, the head 22 of the bone screw 20 can pivot within the thru-bore 12 such that the shank 24 can move freely within multiple planes of motion, as indicated by the cone-shaped shaded area $M_f$. The polyaxial range of motion of the bone screw 20 can vary depending on the particular configuration of the bone screw 20 and the plate 10, for example on the size and shape of the screw head 22 relative to the size and shape of the thru-bore 12, but in the illustrated exemplary embodiment the shank 24 of the bone screw 20 can move approximately 15° in all directions from a neutral axis $A_s$ of the screw 20, such that the cone-shaped shaded area $M_f$ has a cone angle $\alpha_f$ of about 30°. A person skilled in the art will appreciate that the range of motion can be less than or substantially greater than 15° depending on the intended use. For example, the shank 24 of the bone screw 20 can move approximately 10°-20°, and in some cases greater than 25°.

Figure 2A:
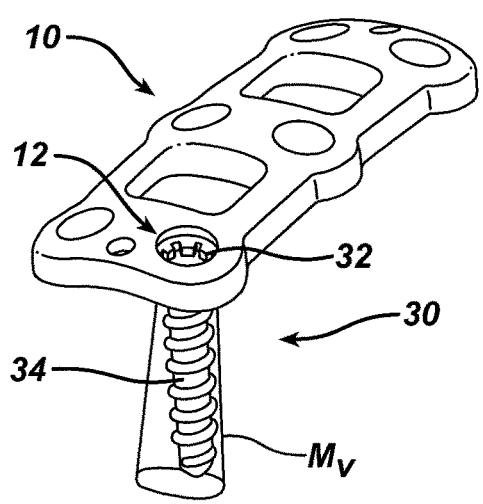
FIG. 2A is a perspective view of the spinal plate shown in FIG. 1A having another exemplary embodiment of a bone screw disposed within a thru-bore formed therein and showing an exemplary range of motion of the bone screw.
Figure 2B:
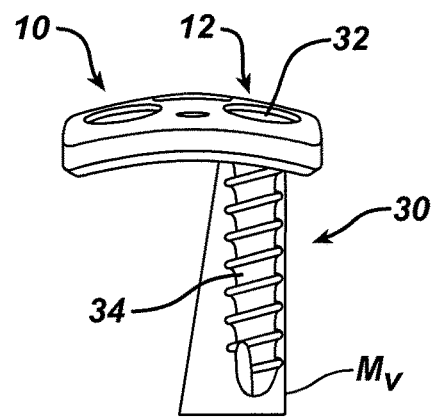
FIG. 2B is an end view of the spinal plate and bone screw shown in FIG. 2A.
Figure 2C:
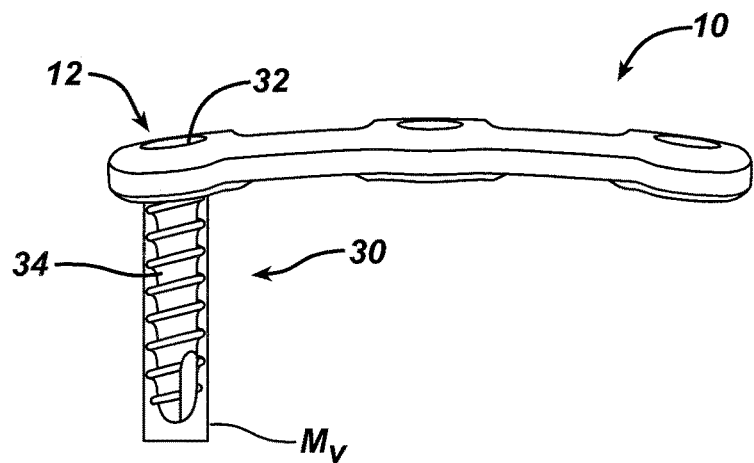
FIG. 2C is a side view of the spinal plate and bone screw shown in FIG. 2A.

Now referring to FIGS. 2A-2C, the spinal plate 10 is shown having a limited angle bone screw 30 disposed within thru-bore 12. Again, the bone screw 30, various exemplary embodiments of which will be discussed in more detail below, generally includes a head 32 and a shank 34 extending from the head 32. In this exemplary embodiment, when the shank 34 of the bone screw 30 is disposed through the thru-bore 12 in the plate 10 and the head 32 of the bone screw 30 is seated within the thru-bore 12, the shank 34 of the bone screw 30 can be substantially limited to movement within a single plane of motion relative to the plate 10. In particular, the head 32 of the bone screw 30 can be configured to pivot within the thru-bore 12 such that the shank 34 has a limited range of motion that can be substantially within a single plane, as indicated by the shaded area $M_l$. The limited range of motion of the bone screw 30 can vary depending on the particular configuration of the bone screw 30 and the plate 10, for example on the size and shape of the screw head 32 relative to the size and shape of the thru-bore 12, but in the illustrated exemplary embodiment the shank 34 of the bone screw 30 can move up to approximately 5° in one direction, i.e., a total of 10° in opposed directions, substantially within a single plane from a neutral axis $A_l$ of the screw 30. A person skilled in the art will appreciate that the range of motion can be less than or substantially greater than 5° depending on the intended use. For example, the range of motion of the shank 34 from the neutral axis of the bone screw 30 can be approximately 5° to approximately 15°. Moreover, while the shank 34 of the bone screw 30 can be substantially limited to movement within a single plane of motion, the bone screw 30 may toggle slightly or have some micro-motion that is outside of the plane of motion, for example, as a result of manufacturing tolerances. It will also be understood that the term "single plane of motion" is intended to generally refer to a direction of movement.

The exemplary spinal plating system shown in FIGS. 1A-3C can be achieved using a variety of techniques. FIGS. 3A-6C illustrate certain exemplary embodiments. A person skilled in the art will appreciate that the exemplary techniques used to achieve a system having two interchangeable fastening elements can be incorporated into a variety of other surgical devices, and that the exemplary spinal plating system disclosed can include a variety of other features known in the art.

Figure 3A:
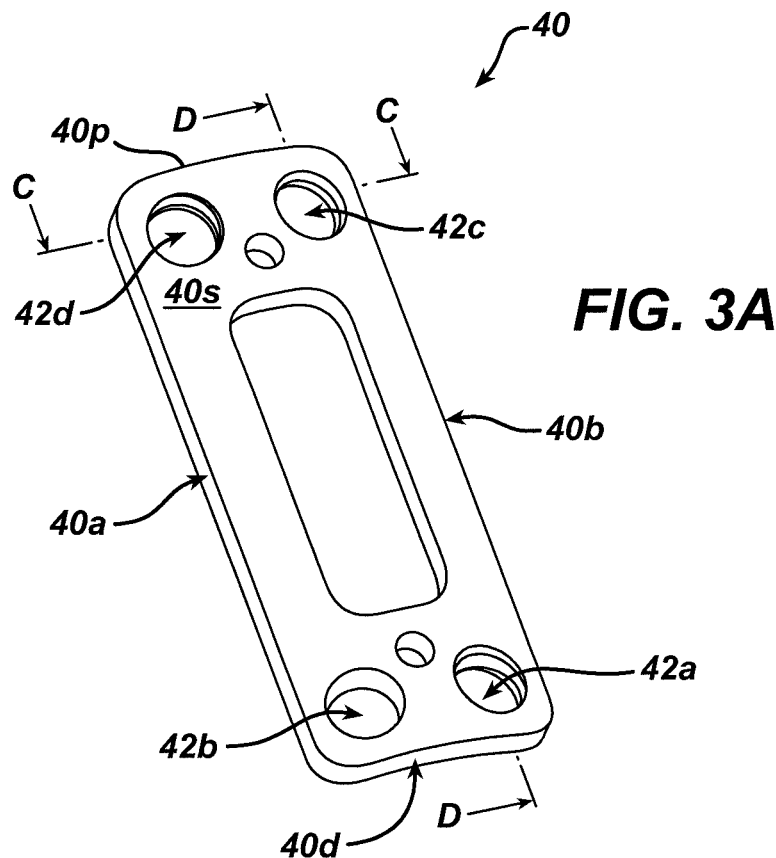
FIG. 3A is a superior perspective view of another exemplary embodiment of a spinal fixation plate.
Figure 3B:
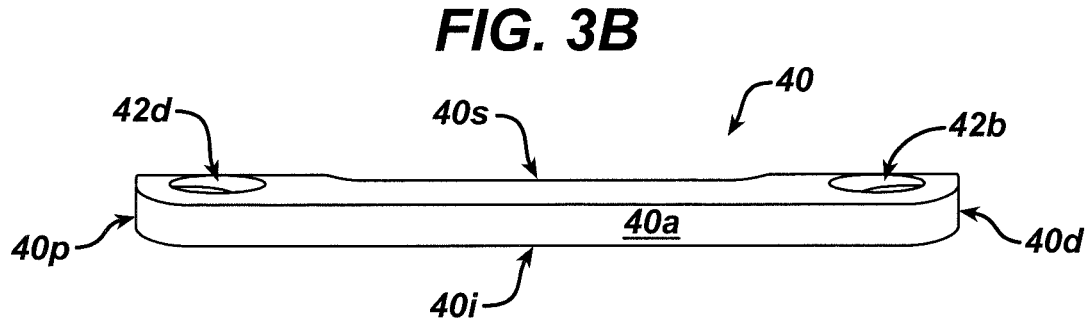
FIG. 3B is a side view of the spinal fixation plate shown in FIG. 3A.
Figure 3C:
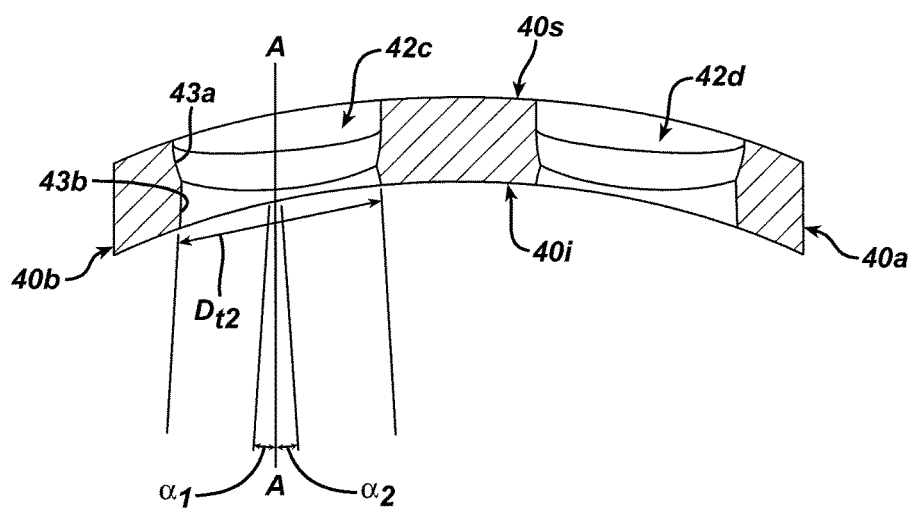
FIG. 3C is a cross-sectional view of the spinal fixation plate shown in FIG. 3A taken across line C-C.
Figure 3D:
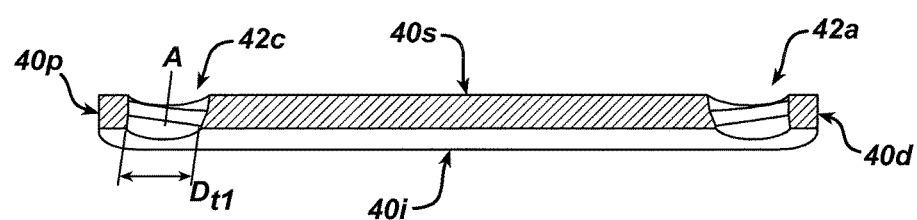
FIG. 3D is a cross-sectional view of the spinal fixation plate shown in FIG. 3A taken across line D-D.
Figure 4A:
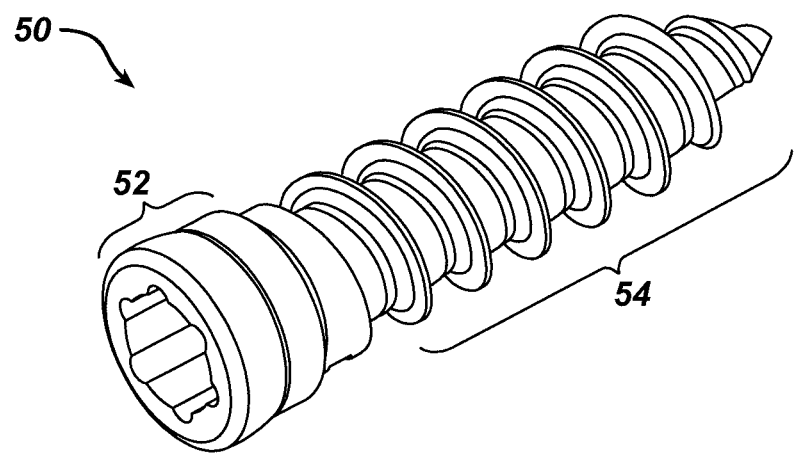
FIG. 4A is a perspective view of one exemplary embodiment of a bone screw adapted to be disposed within one of the thru-bores shown in the spinal fixation plate of FIGS. 3A-3D.
Figure 4B:
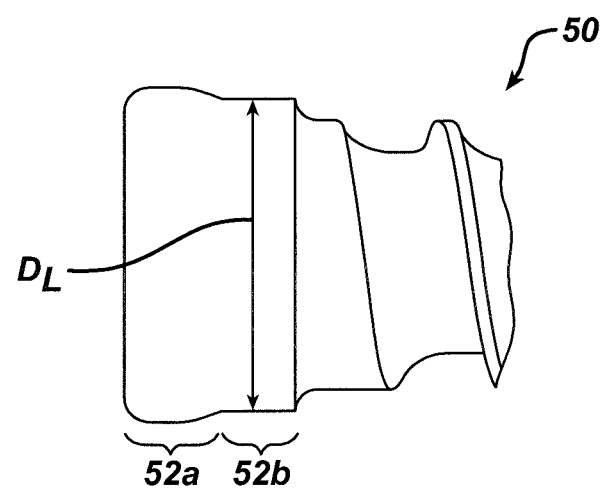
FIG. 4B is an enlarged view of the head of the bone screw shown in FIG. 4A.
Figure 5A:
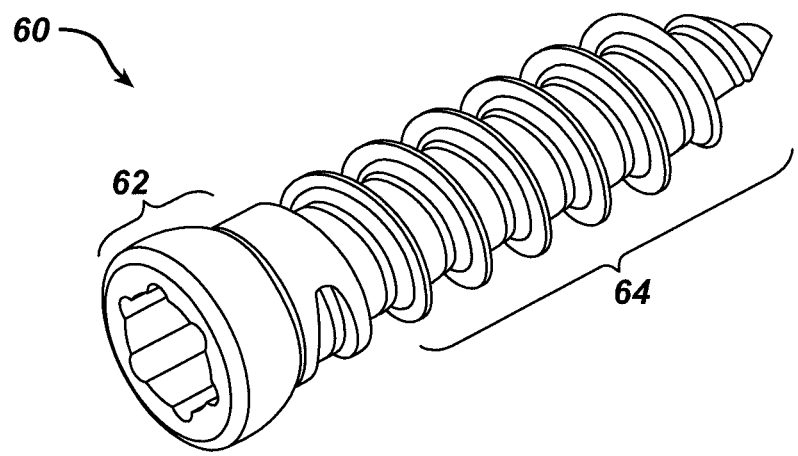
FIG. 5A is a perspective view of another exemplary embodiment of a bone screw adapted to be disposed within one of the thru-bores shown in the spinal fixation plate of FIGS. 3A-3D.
Figure 5B:
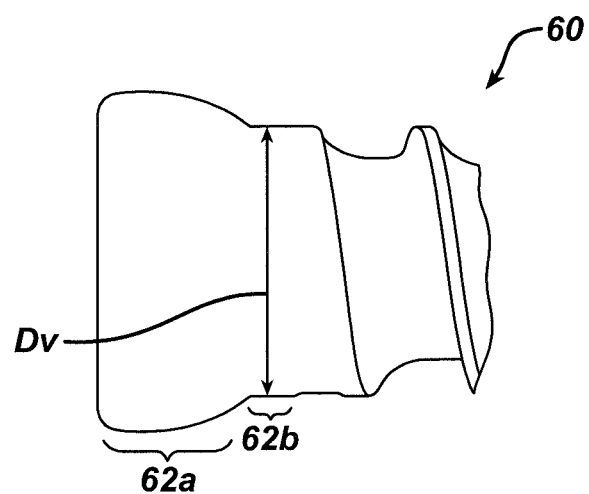
FIG. 5B is an enlarged view of the head of the bone screw shown in FIG. 5A.

Referring first to FIGS. 3A-5B, one exemplary spinal plating system is shown having a fixation plate 40 (shown in FIGS. 3A-3D), a limited angle bone screw 50 (shown in FIGS. 4A-4B), and a variable angle bone screw 60 (shown in FIGS. 5A-5B). While the spinal fixation plate 40 can have virtually any configuration and the illustrated exemplary plate 40 is merely shown for reference purposes only, the exemplary plate 40 has a generally elongate shape with opposed proximal and distal ends 40p, 40d, opposed lateral sides 40a 40b extending between the proximal and distal ends 40p, 40d, a superior non-bone contacting surface 40s, and an inferior bone contacting surface 40i. The plate 40 also includes four thru-bores 42a, 42b, 42c, 42d formed therein and extending between the superior and inferior surfaces 40a, 40b. The plate 40 can, however, include any number of thru-bores. The bone screws 50, 60 can also have a variety of configurations, but in the illustrated exemplary embodiment the bone screws 50, 60 generally include a head 52, 62 and a shank 54, 64 extending distally from the head 52, 62.

In this exemplary embodiment, one or more of the thru-bores 42a, 42b, 42c, 42d in the spinal plate 40 can be adapted interchangeably receive the limited angle bone screw 50 and the variable angle bone screw 60 such that the variable angle bone screw 60 can move polyaxially, as described with respect to FIGS. 1A-1C, while the limited angle bone screw 50 can be substantially limited to movement within a single plane of motion, as described with respect to FIGS. 2A-2C. In one exemplary embodiment, as shown in more detail in FIGS. 3C and 3D, one or more of the thru-bores, e.g., thru-bore 42c, can have a proximal inner wall 43a and a distal inner wall 43b, and the shape of each portion of the inner wall 43a, 43b of the thru-bore 42c can be adapted to interact differently with each bone screw 50, 60. In particular, in the illustrated exemplary embodiment the proximal inner wall 43a of the thru-bore 42c can have a shape that is complementary to the shape of at least a proximal portion of the head 52, 62 of each bone screw 50, 60, while the distal inner wall 43b of the thru-bore 42c can have a shape that differs from the proximal inner wall 43a and that allows free angular movement of the variable angle bone screw 60 while limiting movement of the limited angle bone screw 50.

While the shape of the proximal inner wall 43a of the thru-bore 42c can vary, in one exemplary embodiment the proximal inner wall 43a of the thru-bore 43a can be substantially symmetrical about a common or central axis A of the thru-bore 42c. For example, the proximal inner wall 43a can have a substantially spherical shape. At least a proximal portion 52a, 62a of the head 52, 62 of each bone screw 50, 60 can also have a symmetrical shape, such as a spherical shape as shown in FIGS. 4A-5B, that complements the spherical shape of the proximal inner wall 43a of the thru-bore 42c. Thus, in use, the spherical proximal inner wall 43a of the thru-bore 42c can interchangeably seat the spherical proximal portion 52a, 62a of the head 52, 62 of each bone screw 50, 60, and in an exemplary embodiment the proximal inner wall 43a does not impinge on or otherwise present movement of the proximal portion 52a, 62a of each bone screw 50, 60. A person skilled in the art will appreciate that while the exemplary proximal inner wall 43a is described as having a substantially spherical shape, that the proximal inner wall 43a can have some interruptions in the shape. For example, the proximal inner wall 43a can include a cut-out portion to facilitate use of a locking mechanism with the plate 40, as will be described in more detail below.

The distal inner wall 43b of the thru-bore 42c can also have a variety of shapes and sizes, but in one exemplary embodiment the distal inner wall 43b of the thru-bore 42c is substantially asymmetrical about a common or central axis A of the thru-bore 42c. For example, the distal inner walls 43b of the thru-bore 42c can have an oblong shape, as shown. As a result of the oblong shape of the distal inner wall 43b, the distal inner wall 43b can include a minimum extent $D_{t1}$ and a maximum extent $D_{t2}$ that is greater that minimum extent $D_{t1}$. The minimum and maximum extents $D_{t1}$, $D_{t2}$ can be adapted to control movement of each bone screw 50, 60.

As shown in FIGS. 5A and 5B, the exemplary variable angle bone screw 60 has a head 62 with a distal portion 62b that is adapted to be received within the distal portion 43b of the thru-bore 42c. While the shape of the distal portion 62b of the head 62 can vary, in the illustrated exemplary embodiment the distal portion 62b is substantially cylindrical. The distal portion 62b can have an extent, e.g., a diameter $D_v$, that is substantially less than the minimum and maximum extents $D_{t1}$, $D_{t2}$ of the distal portion 43b of the thru-bore 42c. As a result, the distal portion 62b of the head 62 of the variable angle bone screw 60 can move in multiple directions, e.g., proximal, distal, medial, lateral, and combinations thereof, such that the shank 64 is polyaxial relative to the plate 40. A person skilled in the art will appreciate that the head 62 of the variable angle bone screw 60 does not necessarily need to include a distal portion 62b, and that the head 62 can merely taper into the shank 64.

As shown FIGS. 4A and 4B, the limited angle bone screw 50 can also have a head 52b with a distal portion 52b that is also adapted to be received within the distal portion 43b of the thru-bore 42c. However, in an exemplary embodiment, the distal portion 52b of the head 52 of the limited angle bone screw 50 can differ in size relative to the distal portion 62b of the head 62 of the variable angle bone screw 60. In an exemplary embodiment, the distal portion 52b of the head 52 of the limited angle bone screw 50 has a substantially cylindrical shape with an extent, e.g., a diameter $D_L$, that is greater than an extent, e.g., a diameter $D_v$, of the distal portion 62b of the variable angle bone screw 60, that is substantially less than the maximum extent $D_{t2}$ of the oblong distal inner wall 43b of the thru-bore 42c, and that is only slightly less than the minimum extent $D_{t1}$ of the oblong distal inner wall 43b of the thru-bore 42c. As a result, when the head 52 of the limited angle bone screw 50 is seated within the thru-bore 42c, the portion of the distal inner wall 43b of the thru-bore 42c having a minimum extent $D_{t1}$ can engage the distal portion 52b of the head 52 of the limited angle bone screw 50, thereby preventing movement of the bone screw 50 in the direction of the minimum extent $D_{t1}$. The bone screw 50 can move in the direction of the maximum extent $D_{t2}$ of the distal inner wall 43b of the thru-bore 42c as the maximum extent $D_{t2}$ is greater than the extent, e.g., diameter $D_L$, of the distal portion 52b of the limited angle bone screw 50.

The direction of movement of the limited angle bone screw 50 can vary depending on the positioning of the oblong distal inner wall 43b of the thru-bore 42c. In other words, the minimum and maximum extents $D_{t1}$, $D_{t2}$ of the oblong distal inner wall 43b of the thru-bore 42c can extend in any direction relative to the plate 40 depending on the intended plane of motion of the limited angle bone screw 50. In one exemplary embodiment, the minimum extent $D_{t1}$ extends in a proximal-distal direction, as shown in FIG. 3D, and the maximum extent $D_{t2}$ extends in a side-to-side direction, also referred to as a medial-lateral direction, as shown in FIG. 3C. The limited angle bone screw 50 can thus move freely in a medial-lateral direction, but it can be substantially prevented from moving in a proximal-distal direction.

The amount of movement of each bone screw 50, 60 relative to the plate 40 can also vary, and the size of the head 52, 62 of each bone screw 50, 60, as well as the size of the thru-bore 42c, can be used to control the amount of movement in a particular direction. By way of non-limiting example, at least a portion of the distal inner wall 43b of the thru-bore 42c can be positioned at an angle relative to the central axis A of the thru-bore 42c, and the angle can be determinative of the amount of movement. In the embodiment shown in FIG. 3C, the opposed sides of distal inner wall 43b of the thru-bore 42c that define the maximum extent $D_{t2}$ each extend at angle $\alpha_1$, $\alpha_2$ that is approximately 5° such that the limited angle bone screw 50 can move 5° in a medial direction and 5° in a lateral direction. A person skilled in the art will appreciate that each angle $\alpha_1$, $\alpha_2$ can vary, and that only one or both sides of the distal inner wall 43b of the thru-bore 42c that define the maximum extent $D_{t2}$ can extend at an angle to control movement of the limited angle bone screw 50. Moreover, the distal inner wall 43b of the thru-bore 42c does not need to extend at an angle to control movement of the limited angle bone screw 50. In other exemplary embodiments, some or all of the distal inner wall 43b can be substantially parallel to the central axis A.

For example, the inner wall 43b can have a stepped configuration such that the extent of the inner wall 43b changes between the proximal inner wall 43a and the distal inner wall 43b. In other embodiments, the inner wall 43b can include a series of steps to change the extent between the proximal and distal inner walls 43a, 43b. A person skilled in the art will appreciate that a variety of other techniques can be used to control movement of a limited angle bone screw 50 relative to the plate 40.

Figure 6A:
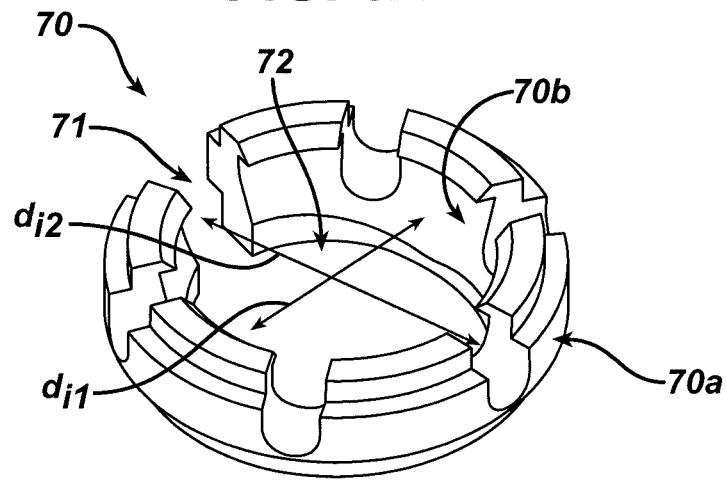
FIG. 6A is a perspective view of an exemplary embodiment of an insert that is adapted to be disposed within a thru-bore in a spinal fixation plate.
Figure 6B:
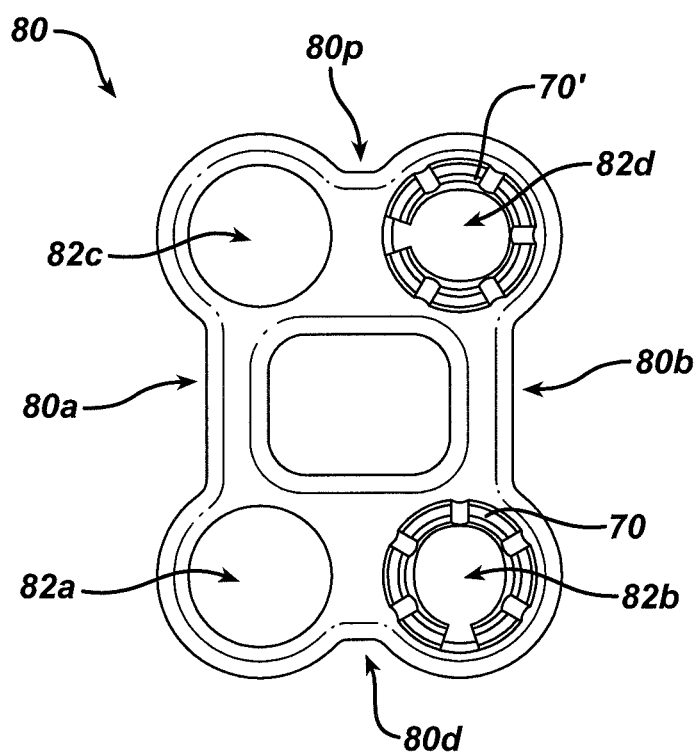
FIG. 6B is a superior view of one embodiment of a spinal fixation plate showing the insert of FIG. 6B disposed within two thru-bores formed therein.
Figure 6C:
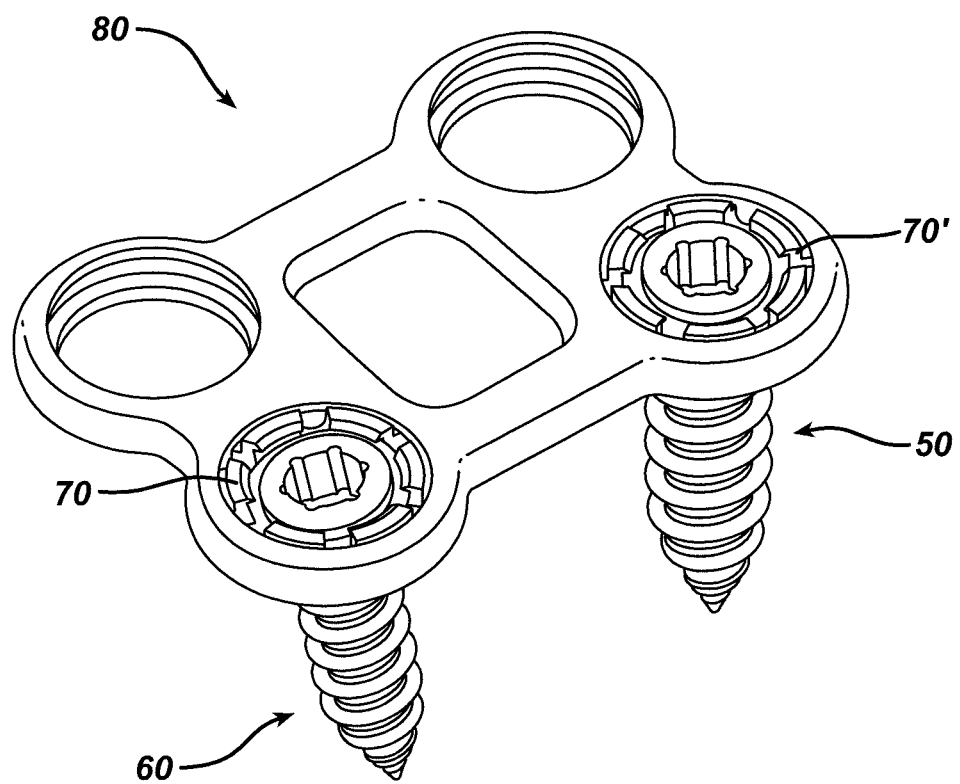
FIG. 6C is a superior view of the spinal fixation plate shown in FIG. 6B showing the insert of FIG. 6B disposed within two thru-bores formed therein and having two bone screws disposed therethrough.

FIGS. 6A-6C illustrate another exemplary embodiment of a spinal plating construct. In this embodiment, rather than having a spinal plate with at least one thru-bore that is adapted to control movement of a variable angle bone screw and a limited angle bone screw, an insert 70 is provided for use with a spinal fixation plate. In one exemplary embodiment, the insert 70 is used with the limited angle bone screw 50 shown in FIGS. 4A-4B and the variable angle bone screw 60 shown in FIGS. 5A-5B. A person skilled in the art will appreciate that the insert 70 can be used with a variety of other fastening devices.

The insert 70 can have virtually any shape and size, but in certain exemplary embodiments the insert 70 can have a shape that is adapted to be received within a thru-bore in a spinal plate. As shown in FIG. 6A, the exemplary insert 70 is substantially ring-shaped with an outer surface 70a and an inner surface 70b defining a bore 72 extending therethrough. As is further shown in FIG. 6A, the exemplary insert 70 can include a split or gap 71 formed therein to allow an extent or size of the insert 70 to be adjusted as may be needed to position the insert within a thru-bore in a spinal plate.

The outer surface 70a of the insert 70 can vary depending on the shape and size of the thru-bore which the insert 70 is adapted to be received within. In the illustrated exemplary embodiment, the outer surface 70a of the insert 70 is substantially cylindrical, but it can have a stepped configuration as shown. The stepped configuration allows the insert 70 to be seated within a thru-bore having a corresponding stepped configuration, thus preventing the insert 70 from passing completely through the thru-bore. An exemplary embodiment of a spinal plate 80 having thru-bores 82a, 82b, 82c, 82d is shown in FIG. 6B, and as shown two inserts 70, 70' are disposed within two of the thru-bores, e.g., thru-bores 82b and 82d. A person skilled in the art will appreciate that the insert 70 can be used with virtually any spinal plate, and plate 80 is merely shown for reference purposes.

The inner surface 70b of the insert 70 can also have a variety of configurations, but in one exemplary embodiment the inner surface 70b is adapted to receive and interact differently with a variable angle bone screw, such as bone screw 60 shown in FIGS. 5A-5B, and a limited angle bone screw, such as bone screw 50 shown in FIGS. 4A-4B. As shown in FIG. 6A, at least a portion of the inner surface 70b of the exemplary insert 70 can be substantially asymmetrical about a common or central axis of the insert 70. In an exemplary embodiment, the inner surface 70b is similar to thru-bore 42c previously described in FIGS. 3A-3D and it can include a proximal portion that is substantially symmetrical about a common axis of the thru-bore 72, and a distal portion that is substantially asymmetrical about the common axis. By way of non-limiting example, the proximal portion can have an spherical shape and the distal portion can having an oblong shape such that the distal portions includes a minimum extent $d_{i1}$ and maximum extent $d_{i2}$ that is greater than the minimum extent $d_{i1}$.

As previously described with respect to the thru-bore 42c in spinal fixation plate 40, the minimum and maximum extent $d_{i1}$, $d_{i2}$ portions can be adapted to control movement of the bone screws 50, 60, which are shown in FIG. 6C disposed through the inserts 70, 70' in the thru-bores 82b, 82d of plate 80. In an exemplary embodiment, the extent, e.g., diameter $D_v$, of the distal portion 62b of the exemplary variable angle bone screw 60 (shown in FIGS. 5A and 5B) can be substantially less than the minimum and maximum extents $d_{i1}$, $d_{i2}$ of the oblong portion of the inner wall 70b of the insert 70. As a result, the distal portion 62b of the head 62 of the variable angle bone screw 60 can move in multiple directions, e.g., proximal, distal, medial, lateral, and combinations thereof, such that the shank 64 is polyaxial relative to the plate 40. In another exemplary embodiment, the extent, e.g., diameter $D_L$, of the distal portion 52b of the head 52 of the limited angle bone screw 50 can be substantially less than the maximum extent $d_{i2}$ of the oblong portion of the inner wall 72b of the insert 70 and only slightly less than the minimum extent $d_{i1}$ of the oblong portion of the inner wall 72b of the insert 70. As a result, when the head 52 of the limited angle bone screw 50 is seated within the insert 70, the minimum extent $d_{i1}$ portion of the inner wall 72B of the insert 70 can engage the distal portion 52b of the head 52 of the limited angle bone screw 50, thereby substantially preventing movement of the bone screw 50 in the direction of the minimum extent $d_{i1}$. The bone screw 50 can move in the direction of the maximum extent $d_{i2}$ of the distal inner wall 72b of the insert 70 as the maximum extent $d_{i2}$ can be greater than the extent, e.g., diameter $D_L$, of the distal portion 52b of the limited angle bone screw 50.

As was previously described with respect to thru-bore 42c in plate 40, the minimum and maximum extents $d_{i1}$, $d_{i2}$ of the oblong inner wall 72b of the insert 70 can be adapted to control the intended plane of motion of the limited angle bone screw 50. For example, at least a portion of the oblong portion of the inner wall 72b of the insert 70 can be positioned at an angle to control the range of motion of the limited angle bone screw 50. A person skilled in the art will appreciate that the shape of bore 72 in the insert 70 can have a variety of other configurations, and that the shape can be adapted in other ways to control the plane of motion of the limited angle bone screw 50 and/or the range of motion.

In another exemplary embodiment of the present invention, the insert 70 can be adapted to allow the direction of motion of the limited angle bone screw 50 to be selectively adjusted. While various techniques can be used to provide such a configuration, in one exemplary embodiment the direction in which the insert 70 is positioned within the thru-bore in the plate can be determinative of the plane of motion of the limited angle bone screw 50. For example, the maximum extent $d_{i2}$ of the inner wall 70b of the insert 70 can be positioned within a thru-bore 82a-d in the plate 80 in a direction of desired movement of the limited angle bone screw 50, as the maximum extent $d_{i2}$ portion of the inner wall can control the direction in which the limited angle bone screw 50 is allowed to move. As shown in FIG. 6A, the maximum extent $d_{i2}$ of the insert 70 is aligned with the slit 71. Thus, when the insert 70 is disposed within one of the thru-bores 82a-d in the plate, the slit 70 can be positioned in the desired direction of movement. A person skilled in the art will appreciate that a slit 71 is not necessary and that a variety of other techniques can be used to indicate the orientation of the insert, including, for example, indicia formed on the insert 70. Moreover, in use, the insert can be oriented as desired either before or after a bone screw is inserter therethrough.

In another embodiment, the insert 70 can include an alignment mechanism formed thereon and adapted to allow the insert 70 to be selectively aligned with the thru-bore in a desired direction of movement. By way of non-limiting example, the alignment mechanism can be one or more ridges, grooves, protrusions, detents, etc., or other features formed on the outer surface 70a of the insert 70, and the inner surface of at least one of the thru-bores 82a-82d in the plate 80 can include corresponding ridges, grooves, protrusions, detents, etc., or other features formed on the inner surface thereof. The insert 70 can thus be inserted into one of the thru-bores 82a-82d in the plate 80 in a desired position, and the alignment mechanism can be effective to maintain the insert 70 in that position, i.e., to prevent rotation of the insert.

In certain exemplary embodiments, the insert 70 can include four protrusions (not shown) formed on the outer surface 70a thereof, and at least one of the thru-bores 82a-d in the plate 80 can include four corresponding detents (not shown) formed therein for receiving the protrusions. The detents or protrusions can be adapted to align the minimum and maximum extents $d_{i1}$, $d_{i2}$ portions of the insert 70 in a particular direction, such as a proximal-distal direction or a medial-lateral direction. As a result, the insert 70 can be disposed within the thru-bore 82a-d in one of several orientations. In the first orientation, the slit 71, which can function as an indicator for the maximum extent $d_{i2}$ which can be aligned with the slit 71, can be positioned toward the proximal end 80p of the plate 80 to allow movement of the limited angle bone screw 50 in a proximal direction, a distal direction, or both a proximal and distal direction. The slit 71 can likewise be positioned in a second, opposed orientation toward the distal end 80d of the plate 80 to likewise allow movement in a proximal direction, a distal direction, or both a proximal and distal direction. In a third orientation, the slit 71 can be positioned toward lateral side 80a of the plate 80 to allow movement of the limited angle bone screw 50 toward lateral side 80a, toward the opposed lateral side 80b, or in both directions, e.g., a medial-lateral or side-to-side direction. Likewise, in the fourth orientation, the slit 71 can be positioned toward lateral side 80b of the plate 80 to allow movement of the limited angle bone screw 50 toward lateral side 80a, toward the opposed lateral side 80b, or in both directions, e.g., a medial-lateral or side-to-side direction. A person skilled in the art will appreciate that a variety of other techniques can be used to allow the direction of movement of the limited angle bone screw 50 to be controlled.

Figure 8:
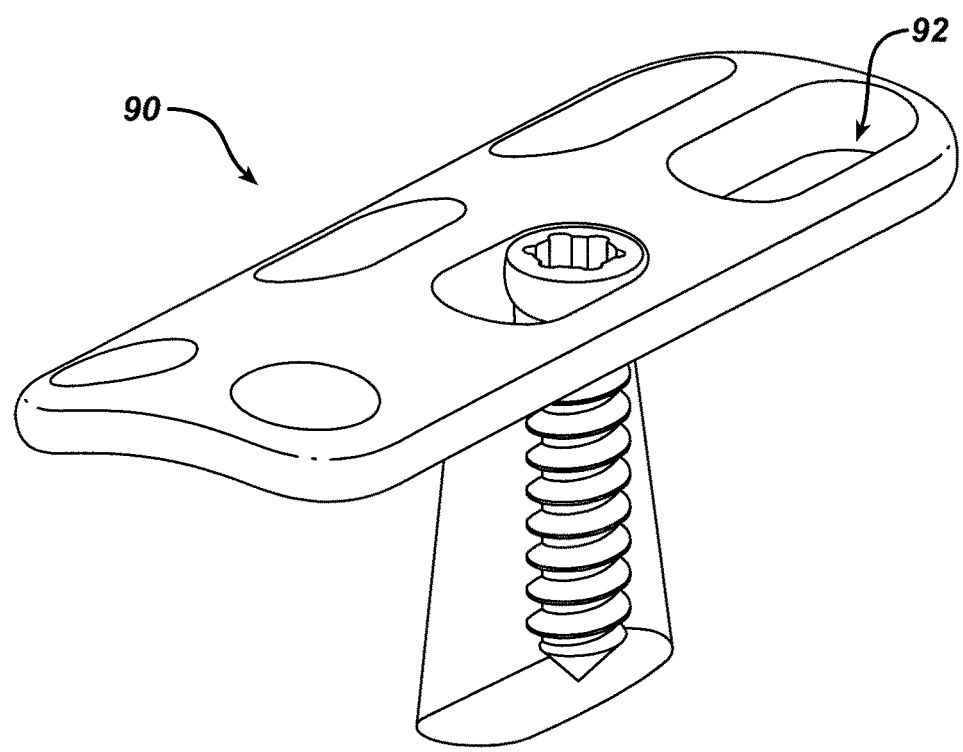
FIG. 8 is a perspective view of yet another embodiment of a spinal fixation plate.

While FIGS. 1A-3D and 6B-6C illustrate various embodiments of spinal fixation plates 10, 40, 50, 60, 80 having thru-bores 12, 42a-d, 82a-d with a generally circular configuration, the thru-bores can have a variety of other shapes. By way of non-limiting example, FIG. 8 illustrates another exemplary embodiment of a spinal fixation plate 90 having a slotted thru-bore 92 formed therein. While not shown, the slotted thru-bore 92 can include features, as previously described, to allow a variable angle bone screw, such as screw 60, to move polyaxially relative to the plate 90, and to substantially limit movement of a limited angle bone screw, such as bone screw 50, to a single plane of motion. The slotted thru-bore 92 can also allow the variable angle bone screw 60 and the limited angle bone screw 50 to translate within the thru-bore 92 to allow a position of the screw 50, 60 to be adjusted relative to the plate 90.

In other exemplary embodiments, a spinal fixation plate can be provided having a thru-bore having a configuration that is substantially opposite to the configuration of the thru-bores 12, 42a-d, 82a-d described above with respect to spinal fixation plates 10, 40, 50, 60, 80. In particular, while not illustrated, an exemplary thru-bore can include a proximal portion that is asymmetrical, e.g., oblong, about a central axis of the thru-bore, and a distal portion that is symmetrical, e.g., spherical shape, about the central axis. An exemplary variable angle bone screw and limited angle bone screw for use with such a thru-b ore can likewise have a reverse orientation, such that a head of the limited angle bone screw includes a proximal portion that is substantially cylindrical and a distal portion that is substantially spherical, and a head of the variable angle bone screw can be substantially spherical. The head of the variable angle bone screw does not necessarily need to include a proximal portion having any particular configuration.

While not illustrated, the various embodiments of the spinal plates disclosed herein can also include a locking or retaining mechanism for preventing bone screw backout. In one embodiment, the locking mechanism can be integrated into the screw head, as described in a U.S. Patent filed on even date herewith and entitled "Locking Bone Screw and Spinal Plate System" of Gorhan et al., which is incorporated by reference herein in its entirety. In another embodiment, the locking mechanism can be integrated onto the surface of the plate. The integrated locking mechanism can be, for example, a cam that is rotatable between an unlocked position and a locked position, in which the cam is forced against the head of the bone screw to provide bone screw backout resistance. An exemplary cam-type locking mechanism is described in U.S. Pat. No. 5,549,612 of Yapp et al. entitled "Osteosynthesis Plate System," which is also incorporated by reference herein in its entirety. Other exemplary retaining or locking mechanisms include, by way of non-limiting example, locking washers, locking screws, and bone screw covers. One skilled in the art will appreciate that various combinations of locking mechanisms can be used as well. Other exemplary locking mechanisms are disclosed in U.S. Pat. No. 6,331,179 to Fried et al., U.S. Pat. No. 6,159,213 to Rogozinski; U.S. Pat. No. 6,017,345 to Richelsoph; U.S. Pat. No. 5,676,666 to Oxland et al.; U.S. Pat. No. 5,616,144 to Yapp et al.; U.S. Pat. No. 5,261,910 to Warden et al.; and U.S. Pat. No. 4,696,290 to Steffee.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A spinal plating system, comprising:
    a spinal plate having a thru-bore extending from a non-bone-contacting surface of the spinal plate to a bone-contacting surface without threading, the thru-bore including a spherical proximal portion and an oblong distal portion and being configured to interchangeably receive variable angle bone screws and limited angle bone screws, the oblong distal portion defining a major diameter and a minor diameter, with the major diameter being larger than the minor diameter, wherein the thru-bore defines a central axis, the spherical proximal portion is symmetric to the central axis, and the oblong distal portion defines a first portion extending away from the central axis in a first direction and a second portion extending away from the central axis in a second direction, the first portion being opposite to the second portion with respect to the central axis and the first and second portions defining the major diameter of the oblong distal portion;
    a variable angle bone screw having a head with a spherical proximal portion and a cylindrical distal portion and a shank extending therefrom, the variable angle bone screw being polyaxially movable with respect to the spinal plate when the variable angle bone screw is seated in the thru-bore; and a limited angle bone screw having a head with a spherical proximal portion and a cylindrical distal portion and a shank extending therefrom, the limited angle bone screw being movable only in a single plane with respect to the spinal plate when the limited angle bone screw is seated in the thru-bore, wherein the cylindrical distal portion of the variable angle bone screw defines a first diameter that is greater than or equal to a maximum diameter of the shank of the variable angle bone screw, and wherein the cylindrical distal portion of the limited angle bone screw defines a second diameter that is greater than the first diameter and less than or equal to the minor diameter.

2. The system of claim 1, wherein the thru-bore permits angulation of the variable angle bone screw up to an angle in the range of 10 and 20 degrees in any direction with respect to the central axis of the thru-bore.

3. The system of claim 1, wherein the thru-bore permits angulation of the limited angle bone screw only up to an angle less than or equal to 5 degrees in the first direction and up to an angle of less than or equal to 5 degrees in the second, opposite direction with respect to the central axis of the thru-bore.

4. A spinal plating system, comprising:
a spinal plate comprising:
a concave distal bone-engaging surface;
a proximal surface opposite to the distal bone-engaging surface; and
at least one thru-bore extending from the proximal surface of the spinal plate to concave distal bone-engaging surface without threading, the thru-bore having a proximal inner wall encircling the thru-bore that is symmetrical about a central axis of the thru-bore and a distal inner wall encircling the thru-bore that is asymmetrical about the central axis, and
first and second bone engaging fasteners, each fastener having a shank portion and a head formed thereon, the head including a spherical proximal portion and a cylindrical distal portion with the shank extending therefrom, wherein the proximal inner wall of the thru-bore is spherical in shape and configured to interchangeably receive the heads of the first and second bone engaging fasteners, and wherein the distal inner wall of the thru-bore is oblong in shape and configured to allow the shank portion of the first bone engaging fastener to move polyaxially with respect to the spinal plate and configured to restrict the shank portion of the second bone engaging fastener to movement in a single plane with respect to the spinal plate, the distal inner wall defining a major diameter and a minor diameter, with the major diameter being larger than the minor diameter, wherein the distal inner wall defines a first portion extending away from the central axis in a first direction and a second portion extending away from the central axis in a second direction, the first portion being opposite to the second portion with respect to the central axis and the first and second portions defining the major diameter of the distal inner wall, wherein the cylindrical distal portion of the first bone engaging fastener defines a first diameter that is greater than or equal to a maximum diameter of the shank of the first bone engaging fastener, and wherein the cylindrical distal portion of the second bone engaging fastener defines a second diameter that is greater than the first diameter and less than or equal to the minor diameter.

5. The system of claim 4, wherein the thru-bore permits angulation of the first bone engaging fastener up to an angle in the range of 10 to 20 degrees in any direction with respect to the central axis of the thru-bore.

6. The system of claim 4, wherein the thru-bore permits angulation of the second bone engaging fastener only up to an angle of less than or equal to 5 degrees in the first direction and up to an angle of less than or equal to 5 degrees in the second, opposite direction with respect to the central axis of the thru-bore.

7. The system of claim 4, wherein the at least one thru-bore comprises a plurality of thru-bores.

8. The system of claim 4, wherein the plate is configured to span a plurality of vertebral levels.

* * * * *